(12) United States Patent
Aqel

(10) Patent No.: US 11,654,251 B2
(45) Date of Patent: May 23, 2023

(54) NEEDLE ASSEMBLY

(71) Applicant: Fadi Aqel, Burbank, IL (US)

(72) Inventor: Fadi Aqel, Burbank, IL (US)

( * ) Notice: Subject to any disclaimer, the term of this patent is extended or adjusted under 35 U.S.C. 154(b) by 0 days.

(21) Appl. No.: 17/721,460

(22) Filed: Apr. 15, 2022

(65) Prior Publication Data

US 2022/0233785 A1 Jul. 28, 2022

Related U.S. Application Data

(63) Continuation of application No. 16/888,518, filed on May 29, 2020, now Pat. No. 11,331,439.

(51) Int. Cl.
*A61M 5/32* (2006.01)
*A61M 5/34* (2006.01)

(52) U.S. Cl.
CPC .......... *A61M 5/329* (2013.01); *A61M 5/3202* (2013.01); *A61M 5/3293* (2013.01); *A61M 5/345* (2013.01); *A61M 5/347* (2013.01)

(58) Field of Classification Search
CPC .... A61M 5/347; A61M 5/329; A61M 5/3293; A61M 5/3202; A61M 5/345; A61M 5/3297; A61M 5/346; A61M 5/3271; A61M 2005/3228; A61M 5/1626; A61M 5/3205; A61M 2005/3208
See application file for complete search history.

(56) References Cited

U.S. PATENT DOCUMENTS

2019/0046735 A1* 2/2019 Ingerslev .............. A61M 5/001

FOREIGN PATENT DOCUMENTS

| FR | 2665079 | * | 1/1992 | .......... A61M 5/3202 |
| WO | 2016116911 | | 7/2016 | |
| WO | WO-2016116911 A1 | * | 7/2016 | .............. A61M 5/32 |

* cited by examiner

*Primary Examiner* — Theodore J Stigell
*Assistant Examiner* — Rachel T. Smith
(74) *Attorney, Agent, or Firm* — The Law Offices of Konrad Sherinian LLC; Depeng Bi

(57) ABSTRACT

A needle assembly includes a needle, a rear needle cap and a front needle cap. The needle includes a needle hub and a needle shaft running through and attached to the needle hub. The shaft incorporates two sharp ends and an internal channel running through the entire length of the shaft. The needle hub includes a rear needle body and a front needle body. The rear needle cap is adapted to be attached to the rear needle body and the front needle cap is adapted to be attached to the front needle body. The front needle body incorporates a guiding channel and a locking receptacle connecting to and extending from the guiding channel in a needle detachment direction. The front needle cap includes an internal locking plug adapted to move along the guiding channel and be disposed inside the locking receptacle. The front needle cap also incorporates a funnel lip.

18 Claims, 3 Drawing Sheets

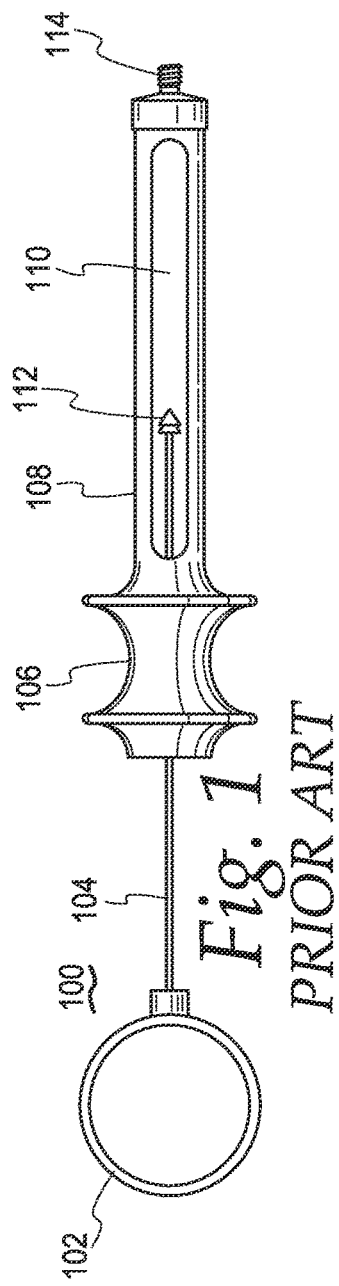
Fig. 1
PRIOR ART
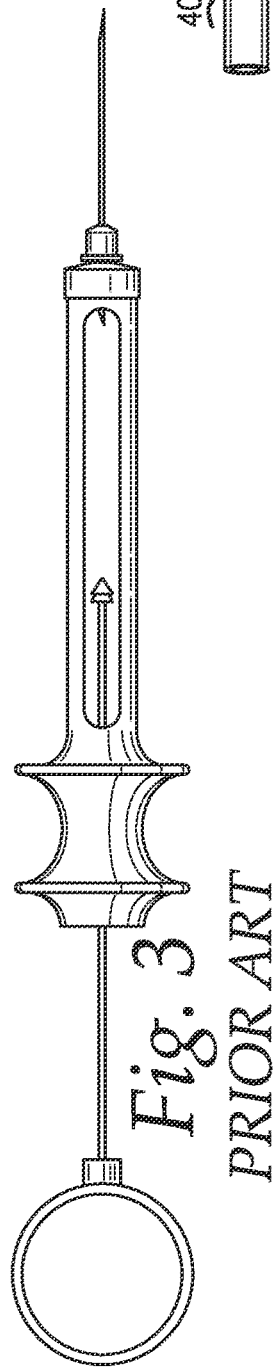
Fig. 3
PRIOR ART
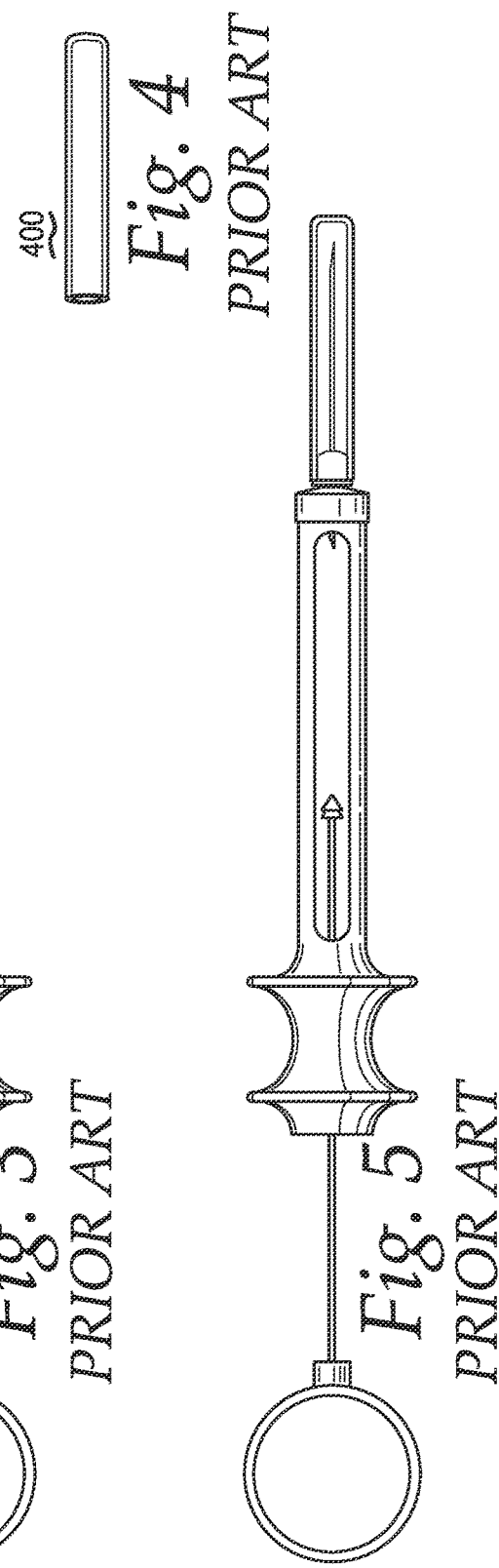
Fig. 2
PRIOR ART
Fig. 4
PRIOR ART
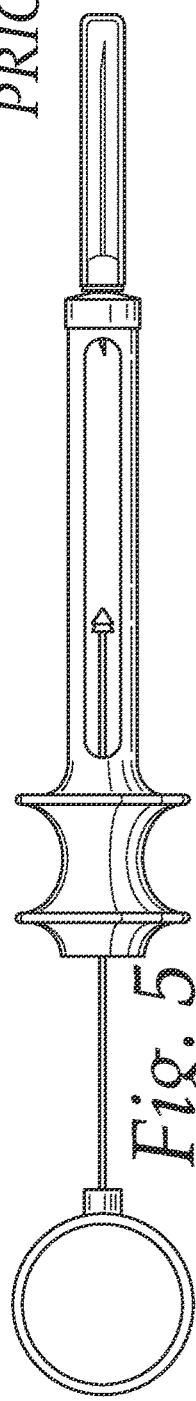
Fig. 5
PRIOR ART

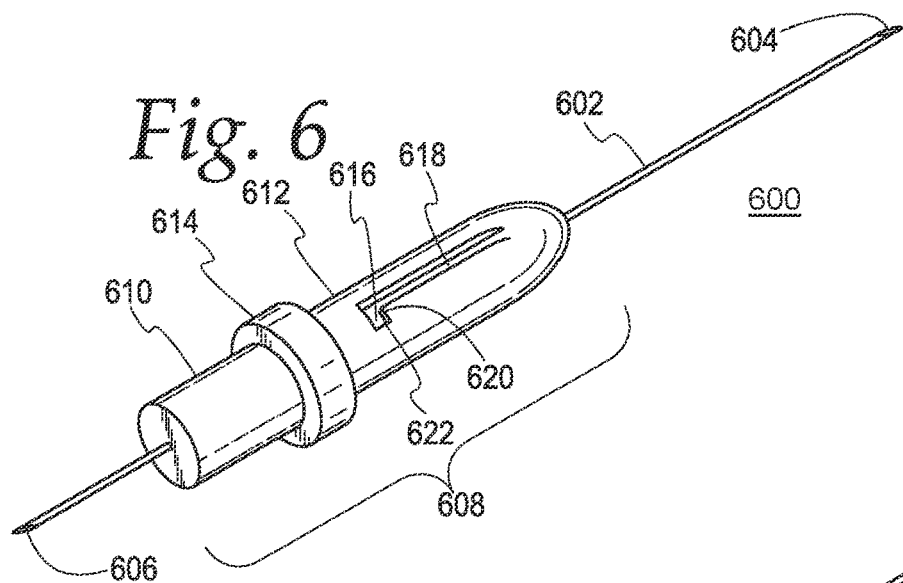
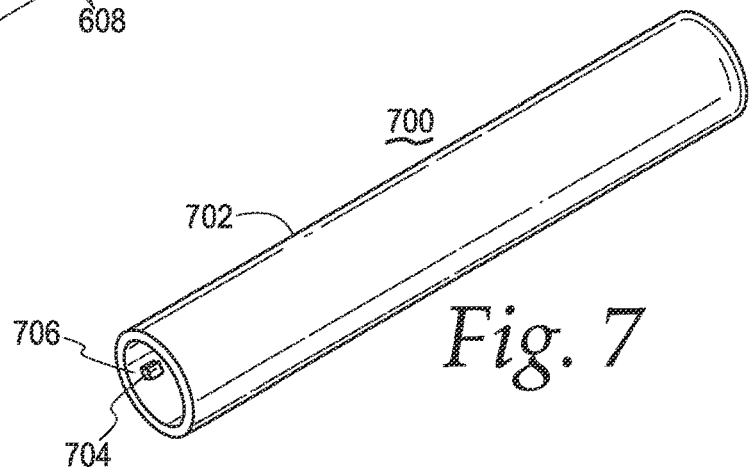
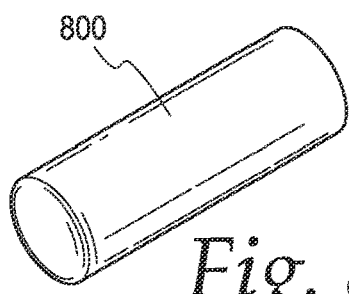
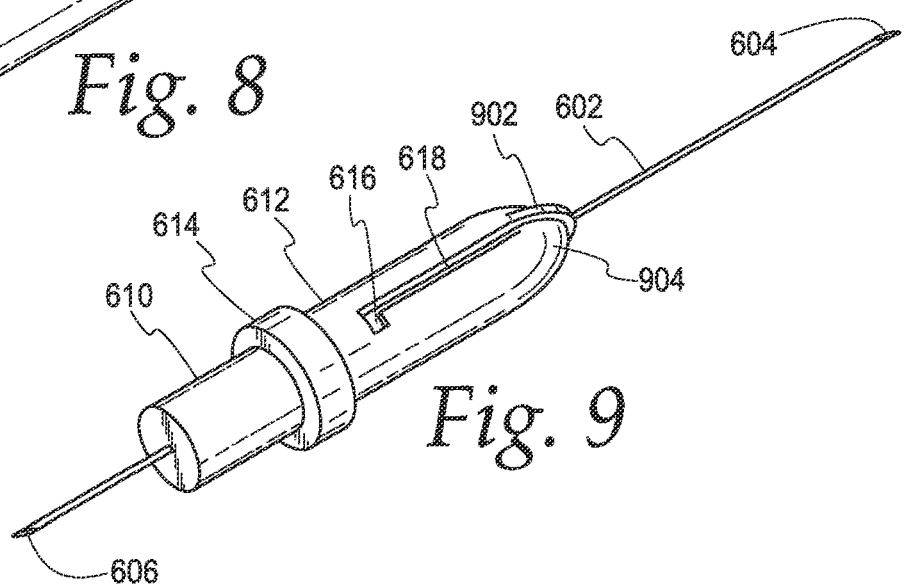

NEEDLE ASSEMBLY

CROSS REFERENCE TO RELATED APPLICATIONS

This application is a continuation of co-pending U.S. patent application Ser. No. 16/888,518, entitled "IMPROVED NEEDLE ASSEMBLY", filed May 29, 2020, which is hereby incorporated by reference in its entirety.

FIELD OF THE DISCLOSURE

The present invention generally relates to medical devices, and more particularly relates to an improved needle assembly. More particularly still, the present disclosure relates to an improved needle assembly used with an aspirating syringe.

DESCRIPTION OF BACKGROUND

Aspirating syringes are widely used in medical and other fields. They are used for both injection and aspiration purposes. Needles are attached to aspirating syringes in practice. A prior art aspirating syringe is shown in FIG. 1 and indicated at 100. The aspirating syringe 100 includes a thumb ring 102, a plunger 104 having a rear end connected to the thumb ring 102, a harpoon 112 at the opposite (front) end of the plunger 104, a finger grip 106, a barrel 108 having a rear end connected to the finger grip 106, an opening 110 on the barrel 108 for receiving a cartridge (not shown), and a needle adaptor 114 at the opposite (front) end of the barrel 108. The plunger 104 is received by an internal cavity of the finger grip 106 and the internal cavity of the barrel 108. A prior art needle is shown in FIG. 2 and indicated at 200. The needle 200 includes a needle hub 206 having a portion that is a front body 208, and a shaft 202 running through the needle hub 206 and a front bevel 204. The aspirating syringe 100 with the needle 200 attached is shown in FIG. 3. A prior art front needle cap is shown in FIG. 4 and indicated at 400.

After the aspirating syringe 100 and the needle 200 are used in a particular medical situation, a user (such as a medical professional) first attaches the front needle cap 400 to the needle hub 206, and then removes the cap 400 and the needle 200 from the syringe 100. This process is also referred to as recapping. To do so, the user needs to align the needle bevel 204 with the opening of the front needle cap 400 before inserting the bevel 204 and the shaft 202 into the internal cavity of the front needle cap 400. Though users are generally very careful with this operation, mishaps do happen when the alignment is not proper and the needle bevel 204 punctures the user's finger or other parts of the user's hand. Since the needle 200 may well have bacteria and/or viruses attached after having been removed from a patient's body, the mishaps can cause disastrous health issues to the user. Accordingly, there is a need for a new type of front needle caps.

After the shaft 202 is inside the front needle cap 400, the user pushes the front needle cap 400 against the needle hub 206 such that the front needle cap 400 receives the entirety of the front body 208. For example, the user uses her/his left hand to hold the barrel 108 and her/his right hand to operate the front needle cap 400. The prior art front needle cap 400 and the prior art front body 208 engage with each other via friction. The front body 208 is in a cylindrical shape.

Once the front needle cap 400 is attached to the front body 208, the user holds the cap 400 and tries to remove the needle 200 away from the aspirating syringe 100. For instance, when the needle adaptor 114 incorporates a thread and the needle hub 206 is attached to the aspirating syringe 100 by threading, the user rotates the front needle cap 400 counterclockwise. At the same time, the user applies some amount of force on the front needle cap 400 to pull it to the right of the user. In such a case, the front needle cap 400 can accidentally become disengaged from the needle body 208 since they are coupled together by friction alone. Furthermore, when the needle 200 is used in, for example, a dental procedure, the front needle body 208 may become wet. For instance, the patient's saliva may wet the front needle body 208. The moisture on the front needle body 208 makes it more likely for the front needle cap 400 to snap off the front needle body 208 while the needle 200 is still attached to the aspirating syringe 100.

The accidental separation of the front needle cap 400 from the needle 200 is more likely to happen to inexperienced users. When it happens, the entirety of the needle bevel 204 can be out of the internal cavity of the front needle cap 400. In the event of the separation, a reflex is likely to happen to the user's right hand holding the front needle cap 400 since a relatively strong force is required to remove the front needle cap 400 that is frictionally engaged with the needle hub 206. In other words, the user's right hand moves leftwards towards the needle bevel 204, and gets punctured by the needle bevel 204. Bacteria and/or viruses on the needle 200 then likely transmit to the user, and cause severe heath harm to her/him. Accordingly, there is a need for a new type of needles. Furthermore, there is a need for a new needle assembly including a needle and a needle cap.

SUMMARY OF THE DISCLOSURE

Generally speaking, pursuant to the various embodiments, the present disclosure provides a needle assembly. The needle assembly includes a needle, which includes a needle hub and a needle shaft disposed within and running through the needle hub. The needle hub includes a rear needle body and a front needle body. The rear needle body includes a needle coupling mechanism adapted for attaching the needle to a syringe needle adaptor. The shaft includes a sharp front end, a sharp rear end and an internal cavity channel extending the entire length of the shaft. The front needle body includes a guiding channel exposed on an outer surface of the front needle body. The front needle body includes a locking receptacle exposed on an outer surface of the front needle body, connecting to a rear end of the guiding channel and extending away from the guiding channel in a needle detachment direction. The needle assembly further includes a rear needle cap adapted to be attached to and enclose the rear needle body, and a front needle cap adapted to be attached to and enclose the front needle body. The front needle cap includes a front needle cap cavity and a locking plug. The locking plug extends away from an inner surface of the front needle cap and into the front needle cap cavity. The locking plug is adapted to move along the guiding channel and be received by the locking receptacle. The front needle cap further incorporates a front funnel lip. The needle coupling mechanism is a female thread or a male thread. The sharp front end is a bevel. The sharp rear end is a bevel. The locking plug and the locking receptacle are in a shape of a prism or a spherical cap.

Further in accordance with the present teachings is a needle assembly. The needle assembly includes a needle having a needle hub and a needle shaft disposed within and running through the needle hub. The needle hub includes a rear needle body and a front needle body. The rear needle body includes a needle coupling mechanism adapted for attaching the needle to a syringe needle adaptor. The shaft includes a sharp front end, a sharp rear end and an internal cavity channel extending the entire length of the shaft. The needle assembly further includes a rear needle cap adapted to be attached to and enclose the rear needle body, and a front needle cap adapted to be attached to and enclose the front needle body. The front needle cap incorporates a front needle cap cavity and a front funnel lip. The needle coupling mechanism is a female thread or a male thread. The sharp front end is a bevel and the sharp rear end is a bevel. The needle hub further includes a cap stopper disposed between the rear needle body and the front needle body.

Further in accordance with the present teachings is a method of assembling a needle assembly for transportation and storage of a needle prior to the needle being attached to and used with a syringe. The needle assembly includes the needle, a rear needle cap, and a front needle cap, the needle having a needle hub and a needle shaft extending along a needle axis. The needle shaft is disposed within and running through the needle hub. The needle hub includes a rear needle body and a front needle body. The rear needle body is adapted for attaching the needle to a syringe needle adaptor. The needle shaft includes a front needle shaft portion, a rear needle shaft portion, and an internal needle cavity channel. The front needle shaft portion extends away from the front needle body in a forward direction and includes a sharp front end. The rear needle shaft portion extends away from the rear needle body in a rearward direction and including a sharp rear end. The internal needle cavity channel extends an entire length of the needle shaft. The front needle body includes a guiding channel and a locking receptacle. The guiding channel and the locking receptacle are exposed on an outer surface of the front needle body. The locking receptacle connects to a rear end of the guiding channel and extending away from the guiding channel in a circumferential needle detachment direction. The front needle cap includes a sidewall, a front wall, an internal cavity extending within the sidewall from the front wall to a rear opening. The front needle cap sidewall has an inner side with an inwardly protruding locking plug formed thereon.

The method includes attaching the rear needle cap to the rear needle body such that the rear needle shaft portion is disposed inside the rear needle cap; inserting the sharp needle front end and the front needle shaft portion into the front needle cap internal cavity; aligning the front needle cap locking plug with the front needle body guiding channel; moving the needle further inside the front needle cap while the locking plug moves inside the guiding channel to move the locking plug to the rear end of the guiding channel, such that the front needle shaft portion is disposed inside the front needle cap; and moving the front needle cap locking plug from the rear end of the guiding channel in a needle detachment direction to move the front needle cap locking plug into the locking receptacle. The needle hub further includes a cap stopper disposed between the rear needle body and the front needle body. The attaching the rear needle cap to the rear needle body includes inserting the sharp needle rear end and the rear needle shaft portion into the rear needle cap and inserting the rear needle body in a rearward direction into the rear needle cap until the rear needle cap operatively engages cap stopper to prevent further rearward insertion of the rear needle body. The front needle body, and the cap stopper have respective diameters. The cap stopper diameter is larger than the rear needle body diameter and larger than the front needle body diameter. The moving the front needle cap locking plug in a needle detachment direction includes moving the front needle cap locking plug along a rearward facing first side of the locking receptacle until the locking plug is against a second side of the locking receptacle. The second side extends in a rearward direction from the first side. The sharp needle front end is a front end needle bevel and the sharp needle rear end is a rear end needle bevel. The guiding channel of the front needle body has an elongate first sidewall, an elongate second sidewall, and a channel bed. The respective lengths of the first and second sidewalls extend parallel to the needle axis. The channel bed extends circumferentially about the front needle body from a radially inner edge of the top wall to a radially inner edge of the bottom wall and axially from a rear end of the channel to a front end of the guiding channel. The second sidewall extends forwardly to a front end at the front end of the guiding channel while the first sidewall extends forwardly to a front end beyond the front end of the guiding channel so that the first sidewall includes a guiding line extending forwardly from the front end of the guiding channel to the front end of the first sidewall. The aligning the front needle cap locking plug with the guiding channel includes moving the front needle cap locking plug against the guiding line and moving the needle forward relative to the front needle cap so that the front needle cap locking plug moves rearwardly along the guiding line to the front end of the guiding channel. The needle detachment direction is counterclockwise about the needle axis in a front view of the needle.

Further in accordance with the present teachings is a method of method of attaching a needle of a needle assembly to a syringe. The needle assembly includes a needle, a rear needle cap, and a front needle cap. The needle includes a needle hub, a needle shaft, and a needle coupling mechanism. The needle shaft is disposed within and running through the needle hub. The needle hub includes a rear needle body and a front needle body. The rear needle body is adapted for attaching the needle to a syringe needle adaptor. The needle shaft includes a rear needle shaft portion, a front needle shaft portion, and an internal needle cavity channel. The rear needle shaft portion extends away from the rear needle body in a rearward direction and includes a sharp rear end. The front needle shaft portion extends away from the front needle body in a forward direction and includes a sharp front end. The internal needle cavity channel extends an entire length of the needle shaft. The front needle body includes a guiding channel and a locking receptacle. The guiding channel and the locking receptacle are exposed on an outer surface of the front needle body. The locking receptacle connects to a rear end of the guiding channel and extends away from the guiding channel in a circumferential needle detachment direction. The rear needle cap is attached to the rear needle body such that the sharp needle rear end is disposed inside the rear needle cap. The front needle cap includes a sidewall, a front wall, an internal cavity extends within the sidewall from the front wall to a rear opening. The front needle cap sidewall has an inner side with an inwardly protruding locking plug formed thereon. The front needle cap is attached to the front needle body such that the sharp needle front end is disposed inside the front needle cap internal cavity and the locking plug of the front needle cap is disposed within the locking receptacle of the front needle body. The syringe includes a barrel and a syringe needle adaptor at a front end of the barrel. The syringe needle adaptor has an internal channel extends from a rear end to a front end of the syringe needle adaptor, and the needle coupling mechanism is adapted for attaching the needle to the syringe needle adaptor for use of the needle with the syringe.

The method includes removing the rear needle cap from the rear needle body; inserting the sharp needle rear end into the syringe needle adaptor internal channel; rotating the front needle cap in an attachment direction relative to the syringe barrel, the attachment direction being opposite to the detachment direction, to cause the needle coupling mechanism to rotate in the attachment direction relative to the syringe needle adaptor to attach the needle to the syringe needle adaptor, and to cause the front needle cap to rotate in the attachment direction relative to the front needle body such that the locking plug is aligned with the guiding channel of the front needle body; pulling the front needle cap forwardly away from the needle with the locking plug moving inside the guiding channel to detach the front needle cap from the front needle body; and continuing to pull the front needle cap forwardly away from the needle to remove the sharp needle front end from the front needle cap. The syringe is an aspirating syringe. The causing the front needle cap to rotate in the attachment direction relative to the front needle body is performed after the needle is attached to the syringe needle adapter by the causing the needle coupling mechanism to rotate in the attachment direction relative to the syringe needle adaptor. The locking plug and the locking receptacle have the same or substantially the same shape for tight interlocking. The needle coupling mechanism is formed in the rear needle body. The needle coupling mechanism is a female thread; and the coupling the needle coupling mechanism to the syringe needle adaptor includes threading the female thread onto a male thread of the syringe needle adaptor. The needle coupling mechanism is a clockwise thread and the attachment direction is clockwise.

Further in accordance with the present teachings is a method of disposing of a used needle attached to a syringe. The syringe includes a barrel has a front end and a syringe needle adaptor at the front end of the barrel. The needle includes a needle hub and a needle shaft. The needle shaft is fixedly disposed within and running through the needle hub. The needle hub includes a rear needle body and a front needle body. The needle shaft includes front needle shaft portion extends forwardly from the front needle body and includes a sharp needle front end, a rear needle shaft portion extending rearwardly from the rear needle body and includes a sharp needle rear end, and an internal cavity channel extending an entire length of the shaft. The rear needle body is detachably attached to the syringe needle adaptor so that the rear end needle shaft portion extends into a front opening of an internal channel extends through the syringe needle adaptor. The front needle body includes a guiding channel and a locking receptacle. The guiding channel and the locking receptacle are exposed on an outer surface of the front needle body. The locking receptacle connects to a rear end of the guiding channel and extends away from the guiding channel in a needle detachment direction.

The method includes, after the needle has been used to penetrate into a patient's body and then removed from the patient's body, inserting the sharp needle front end and the front end portion of the needle shaft through a rear opening and into an internal cavity of a front needle cap, the front needle cap including a sidewall and a front wall, the internal cavity extending within the sidewall from the front wall to the rear opening, the sidewall having an inner side with an inwardly protruding locking plug formed thereon; aligning the front needle cap locking plug with the front needle body guiding channel; moving the needle further inside the front needle cap while the locking plug moves inside the guiding channel to move the locking plug to the rear end of the guiding channel; rotating the front needle cap in a needle detachment direction relative to the syringe barrel so as to move the locking plug from the rear end of the guiding channel into the locking receptacle and along a rearward facing first side of the locking receptacle until the locking plug is against a second side of the locking receptacle, the second side extending in a rearward direction from the first side; and continuing to rotate the front needle cap in the needle detachment direction so that the locking plug drives the needle hub to rotate in the detachment direction relative to the syringe needle adaptor until the rear needle body is detached from the syringe needle adaptor. The method further includes pulling the front needle cap forwardly away from the syringe needle adaptor to remove the needle shaft rear end portion from the internal channel of the syringe needle adaptor, inserting the sharp needle rear end into a rear needle cap, and attaching the rear needle cap to the rear needle body so that the sharp needle rear end is disposed inside the rear needle cap. The method further includes the rearward facing first side of the locking receptacle restraining forward movement of the locking plug while the locking plug is in the locking receptacle. The method further includes the needle detachment direction being counterclockwise with respect to a front end view of the syringe needle adaptor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Although the characteristic features of this disclosure will be particularly pointed out in the claims, the invention itself, and the manner in which it may be made and used, may be better understood by referring to the following description taken in connection with the accompanying drawings forming a part hereof, wherein like reference numerals refer to like parts throughout the several views and in which:

FIG. 1 is a perspective view of a prior art aspirating syringe.

FIG. 2 is a perspective view of a prior art needle for an aspirating syringe.

FIG. 3 is a perspective view of a prior art aspirating syringe with a prior art needle attached.

FIG. 4 is a perspective view of a prior art front needle cap.

FIG. 5 is a perspective view of a prior art aspirating syringe with a prior art needle and a prior art front needle cap attached.

FIG. 6 is a front perspective view of a new needle in accordance with the present teachings.

FIG. 7 is a front perspective view of a new front needle cap in accordance with this disclosure.

FIG. 8 is a front perspective view of a rear needle cap in accordance with this disclosure.

FIG. 9 is a front perspective view of a new needle in accordance with this disclosure.

Figure 10:
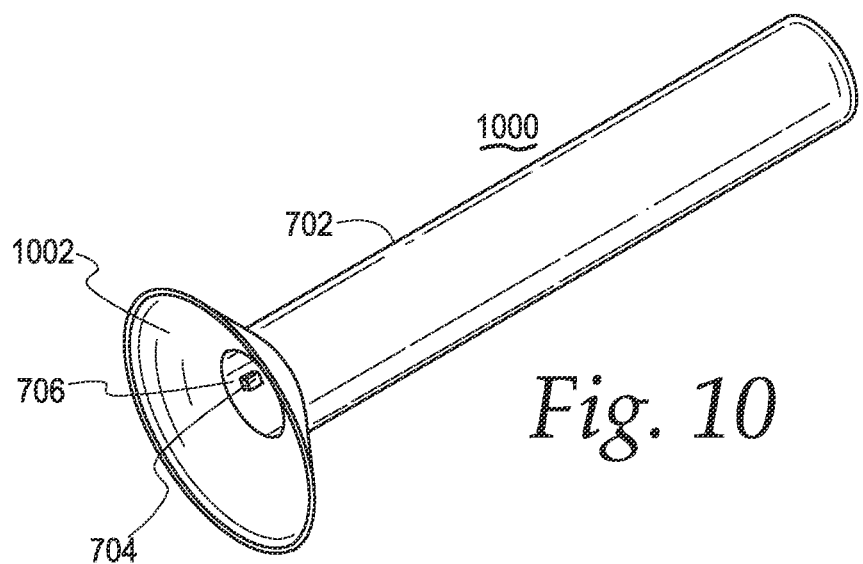
FIG. 10 is a front perspective view of a new front needle cap in accordance with this disclosure.

A person of ordinary skills in the art will appreciate that elements of the figures above are illustrated for simplicity and clarity, and are not necessarily drawn to scale. The dimensions of some elements in the figures may have been exaggerated relative to other elements to help understanding of the present teachings. Furthermore, a particular order in which certain elements, parts, components, modules, steps, actions, events and/or processes are described or illustrated may not be actually required. A person of ordinary skill in the art will appreciate that, for the purpose of simplicity and clarity of illustration, some commonly known and well-understood elements that are useful and/or necessary in a commercially feasible embodiment may not be depicted in order to provide a clear view of various embodiments in accordance with the present teachings.

DETAILED DESCRIPTION

Turning to the Figures and to FIG. 6 in particular, an illustrative diagram of a new needle is shown and generally indicated at 600. The needle 600 includes a shaft 602, a front end needle bevel 604 at a front end of the shaft 602, a rear end needle bevel 606 at a rear end of the shaft 602, and a needle hub 608. The shaft 602 extends through and is firmly attached to the needle hub 608. The shaft 602 does not move inside the needle hub 608. The bevel 604 is adapted to penetrate into the body of a patient. The bevel 606 is adapted to penetrate into the cover of a cartridge adapted to be disposed inside the barrel 108. Internal cavity of the barrel 108 is exposed by the opening 110. The shaft 602 incorporates an internal channel running through the entire length of the shaft 602 and through the bevels 604-606 for transmitting liquid. The bevels 604-606 are generally referred to herein as sharp ends of the needle 600.

The needle hub 608 includes a portion that is a rear needle body 610, a portion that is a front needle body 612 and a cap stopper 614 between the rear and front needle bodies 610-612. In one implementation, the rear needle body 610, the front needle body 612 and the cap stopper 614 are integrally formed. Alternatively, they are separate parts coupled together via, for example, threading or welding.

The rear end needle bevel 606 and the rear needle body 610 are adapted to be received by and disposed inside a rear needle cap, such as the rear needle cap 800 shown in FIG. 8. When the needle 600 is in transportation, storage and waiting to be used, the rear needle cap 800 is attached to the needle 600 to protect the rear portion of the shaft 602 extending away from the rear needle body 610.

In addition, the needle 600 incorporates a needle coupling mechanism for attaching the needle 600 to an aspirating syringe, such as the syringe 100. In one implementation, the rear needle body 610 incorporates a female thread for receiving the needle adaptor. In such a case, a user of the needle 600 carefully inserts the bevel 606 into an internal channel of the needle adaptor 114 and then firmly attaches the needle 600 to the syringe 100 via the threads of the needle adaptor 114 and the female threads of the rear needle body 610. A left side view of the shaft 602 and the rear needle body 610 is shown in FIG. 12.

Figure 12:
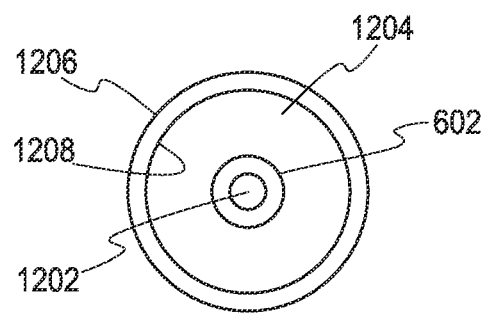
FIG. 12 is a left side view of a new needle in accordance with this disclosure.

Referring to FIG. 12, the internal cavity channel of the shaft 602 is indicated at 1202. The outer surface of the rear needle body 610 is indicated at 1206 while the inner surface of the rear needle body 610 is indicated at 1208. The cavity adapted for receiving the needle adaptor 114 is indicated at 1204. The female thread of the rear needle body 610 is incorporated on the inner surface 1208. The cavity 1204 does not run through the entirety of the needle hub 608. Instead, its depth is properly configured to receive the needle adaptor 114.

Turning back to FIG. 6, the front needle body 612 is adapted to be received by a new front needle cap 700 shown in FIG. 7. When the needle 600 is in transportation or waiting to be used, the cap 700 is attached to the needle 600. In particular, the cap 700 is attached to and encloses the front needle body 612. At this position, the front shaft portion extending away from the front needle body 612 and the bevel 604 are disposed inside the internal cavity 706 of the front needle cap 700. The cap stopper 614 incorporates a larger diameter than those of the needle bodies 610-612 to prevent the caps 700-800 from enclosing too much of the needle hub 608 to damage the bevels 604-606.

The improved needle 600 further incorporates a guiding channel 618 extending along the front needle body 612 and exposed on the outer surface of the front needle body 612, and a locking receptacle 616 at the rear end of the guiding channel 618 and exposed on the outer surface of the front needle body 612. The locking receptacle 616 communicates with and extends from the guiding channel 618.

Referring to FIG. 7, a perspective view of the improved front needle cap 700 is shown. The front needle cap 700 includes a cap body 702 enclosing the internal cavity 706 for receiving the front needle body 612 and the needle shaft 602. The front needle cap 700 further incorporates a locking plug 704 extending from the inner surface of the cavity 706 toward the center axis of the cavity 706.

The locking plug 704 is adapted to move along the guiding channel 618 and be disposed inside the locking receptacle 616. When the front needle cap 700 is attached to the needle 600, the locking plug 704 is received by the locking receptacle 616. The locking plug 704 and the locking receptacle 616 have the same or substantially the same shape for tight interlocking. For example, they are in the shape of a prism. As another example, the locking receptacle 616 and the locking plug 704 are spherical caps.

After a user attaches the needle 600 to the needle adaptor 114 for using the needle 600, the user slightly turns the front needle cap 700 clockwise such that the locking plug 704 is aligned with the guiding channel 618. The user then pulls the front needle cap 700 away from the needle 600 with the locking plug 704 moving inside the guiding channel 618. At this point, the needle 600 is ready for use, such as in a dental procedure.

After the use is over, the user attaches the front needle cap 700 back to the needle 600. To do so, she/he first inserts the bevel 604 and the shaft 602 into the cavity 706. Then, she/he aligns the locking plug 704 with the guiding channel 618 before moving the needle 600 further inside the front needle cap 700 while the locking plug 704 moves inside the guiding channel 618. Once the locking plug 704 reaches the end of the guiding channel 618, she/he slightly rotates the front needle cap 700 counterclockwise such that the locking plug 704 is disposed inside the locking receptable 616 and no longer aligned with the guiding channel 618.

Thereafter, the user continues to rotate the front needle cap 700 counterclockwise while firmly holding the barrel 108 by a different hand. The rotation unscrews the needle 600 from the needle adaptor 114. During the removal process, the interlocking between the locking receptacle 616 and the locking plug 704 avoids the front needle cap 700 from being removed from the needle hub 608. Accordingly, the interlocking mechanism prevents the accidental separation between the front needle cap 700 and the needle 600 right during the recapping process after the needle 600 is used in a procedure.

The locking receptacle 616 includes a side 620 extending away from the guiding channel 618. The direction by which the side 620 extends away from the guiding channel 618 needs to be in the same direction by which the needle 600 is rotated to be detached from the aspirating syringe 100. The direction can be clockwise or counterclockwise, depending on the commercial embodiments. The direction is termed herein as a needle detachment direction. Accordingly, the side 620 of the locking receptacle 616 is said to extend from the guiding channel 618 in the needle detachment direction. The locking receptacle 616 itself is also said to extend from the guiding channel 618 in the needle detachment direction. During the recapping of the needle 600, the locking plug 704 is against a bottom side 622 of the locking receptacle 616. Therefore, the side 620 prevents the locking plug 704 from moving away from the front needle body 612.

In a further implementation, the front needle body 612 incorporates a tapered front end 904 shown in FIG. 9. In such a case, a guiding line 902 is provided on the tapered front end 904. The guiding line 902 is aligned with the top edge of the guiding channel 618. The guiding line 902 assists the user to align the locking plug 704 with the guiding channel 618. Furthermore, the guiding line 902 has a decreasing height toward the cylindrical portion of the front needle body 612 such that the guiding line 902 does not increase the outer diameter or circumference of the cylindrical portion of the front needle body 612.

When the locking plug 704 is disposed inside the locking receptacle 616, the front needle cap 700 cannot move along the shaft 602. The cap stopper 614 is thus not required to practice the present teachings. In other words, with the interlocking mechanism, the present teaching can be practiced without cap stopper 614.

When the user attaches the front needle cap 700 to the needle 600 after its use, she/he still needs to carefully align the sharp front end 604 of the shaft 602 with the cavity 706. A mistake in aligning them can cause the sharp front end 604 to puncture the user's hand and lead to serious heath harm to the user. One conventional solution is that the user attaches the cap 400 to a flat object (such as a square board) through an aperture in the flat object. The flat object has a much larger length and width than the diameter of the cap 400. The user then holds the flat object to align the cap 400 with the sharp end 204 of the needle 200 to avoid accidental puncture by the needle.

Figure 11:
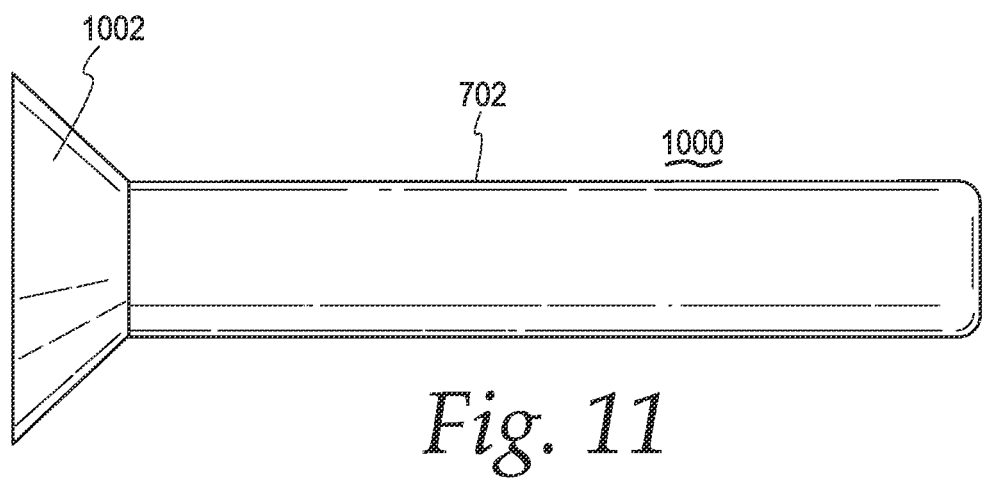
FIG. 11 is a front side view of a new front needle cap in accordance with this disclosure.

An improved front needle cap shown in FIGS. 10-11 solves the problem and avoids the need of the flat object. Turning to FIG. 10, a perspective of an improved front needle cap is shown and generally indicated at 1000. The improved front needle cap 1000 takes the shape of a filling funnel on its opening end. The front circular funnel lip 1002 provides a larger diameter than that of the cavity 706, makes the alignment between the cavity 706 and the needle end 604 easier, and avoids accidental puncture of the user's hand by the sharp end 604 during recapping of the needle 600.

As used herein, the needle 600, the front needle cap 700 and the rear needle cap 800 are collectively referred to as a needle assembly. The needle 600, the front needle cap 1000 and the rear needle cap 800 are a different needle assembly. Needle assemblies are each packaged together and provided to users. Accordingly, the present teachings provide improved needle assemblies.

Obviously, many additional modifications and variations of the present disclosure are possible in light of the above teachings. Thus, it is to be understood that, within the scope of the appended claims, the disclosure may be practiced otherwise than is specifically described above. For example, the funnel lip 1002 can be at different angles to the center axis of the front needle cap body 702. As an additional example, the height of the funnel lip 1002 can vary. As still a further example, when the needle adaptor 114 includes a female thread, the needle hub 608 includes a male thread for attaching the needle 600 to the aspirating syringe 100.

The foregoing description of the disclosure has been presented for purposes of illustration and description and is not intended to be exhaustive or to limit the disclosure to the precise form disclosed. The description was selected to best explain the principles of the present teachings and practical application of these principles to enable others skilled in the art to best utilize the disclosure in various embodiments and various modifications as are suited to the particular use contemplated. It should be recognized that the words "a" or "an" are intended to include both the singular and the plural. Conversely, any reference to plural elements shall, where appropriate, include the singular.

It is intended that the scope of the disclosure not be limited by the specification but be defined by the claims set forth below. In addition, although narrow claims may be presented below, it should be recognized that the scope of this invention is much broader than presented by the claim (s). It is intended that broader claims will be submitted in one or more applications that claim the benefit of priority from this application. Insofar as the description above and the accompanying drawings disclose additional subject matter that is not within the scope of the claim or claims below, the additional inventions are not dedicated to the public and the right to file one or more applications to claim such additional inventions is reserved.

What is claimed is:

1. A method of assembling a needle assembly for transportation and storage of a needle prior to the needle being attached to and used with a syringe, the needle assembly comprising the needle, a rear needle cap, and a front needle cap, the needle having a needle hub and a needle shaft extending along a needle axis, said needle shaft being disposed within and running through said needle hub, said needle hub including a rear needle body and a front needle body, said rear needle body being adapted for attaching said needle to a syringe needle adaptor, said needle shaft including a front needle shaft portion, a rear needle shaft portion, and an internal needle cavity channel, the front needle shaft portion extending away from the front needle body in a forward direction and including a sharp front end, the rear needle shaft portion extending away from the rear needle body in a rearward direction and including a sharp rear end, said internal needle cavity channel extending an entire length of said needle shaft, said front needle body including a guiding channel and a locking receptacle, said guiding channel and said locking receptacle being exposed on an outer surface of said front needle body, said locking receptacle connecting to a rear end of said guiding channel and extending away from said guiding channel in a circumferential needle detachment direction, the front needle cap comprising a sidewall, a front wall, an internal cavity extending within the sidewall from the front wall to a rear opening, the front needle cap sidewall having an inner side with an inwardly protruding locking plug formed thereon, the method comprising:
attaching the rear needle cap to the rear needle body such that the rear needle shaft portion is disposed inside the rear needle cap;
inserting the sharp needle front end and the front needle shaft portion into the front needle cap internal cavity;
aligning the front needle cap locking plug with the front needle body guiding channel;

moving the needle further inside the front needle cap while the locking plug moves inside the guiding channel to move the locking plug to the rear end of the guiding channel, such that the front needle shaft portion is disposed inside the front needle cap; and moving the front needle cap locking plug from the rear end of the guiding channel the circumferential needle detachment direction to move the front needle cap locking plug into the locking receptacle.

2. The method of claim 1, wherein said needle hub further comprises a cap stopper, the cap stopper being disposed between said rear needle body and said front needle body, and said attaching the rear needle cap to the rear needle body comprises inserting the sharp needle rear end and the rear needle shaft portion into the rear needle cap and inserting the rear needle body in a rearward direction into the rear needle cap until the rear needle cap operatively engages cap stopper to prevent further rearward insertion of the rear needle body.

3. The method of claim 2, wherein said rear needle body, said front needle body, and said cap stopper have respective diameters, the cap stopper diameter being larger than the rear needle body diameter and larger than the front needle body diameter.

4. The method of claim 1, wherein said moving the front needle cap locking plug in the circumferential needle detachment direction comprises moving the front needle cap locking plug along a rearward facing first side of the locking receptacle until the locking plug is against a second side of the locking receptacle, the second side extending in a rearward direction from the first side.

5. The method of claim 1, wherein the sharp needle front end is a front end needle bevel and the sharp needle rear end is a rear end needle bevel.

6. The method of claim 1, wherein the guiding channel of the front needle body has an elongate first sidewall, an elongate second sidewall, and a channel bed, the respective lengths of the first and second sidewalls extending parallel to the needle axis, the channel bed extending circumferentially about the front needle body from a radially inner edge of the top wall to a radially inner edge of the bottom wall and axially from a rear end of the channel to a front end of the guiding channel, the second sidewall extending forwardly to a front end at the front end of the guiding channel, and the first sidewall extending forwardly to a front end beyond the front end of the guiding channel so that the first sidewall comprises a guiding line extending forwardly from the front end of the guiding channel to the front end of the first sidewall, wherein said aligning the front needle cap locking plug with the guiding channel comprises moving the front needle cap locking plug against the guiding line and moving the needle forward relative to the front needle cap so that the front needle cap locking plug moves rearwardly along the guiding line to the front end of the guiding channel.

7. The method of claim 1, wherein said needle detachment direction is counterclockwise about the needle axis in a front view of the needle.

8. A method of attaching a needle of a needle assembly to a syringe, the needle assembly comprising a needle, a rear needle cap, and a front needle cap, the needle comprising a needle hub, a needle shaft, and a needle coupling mechanism, said needle shaft being disposed within and running through said needle hub, said needle hub including a rear needle body and a front needle body, said rear needle body being adapted for attaching said needle to a syringe needle adaptor, said needle shaft including a rear needle shaft portion, a front needle shaft portion, and an internal needle cavity channel, the rear needle shaft portion extending away from the rear needle body in a rearward direction and including a sharp rear end, the front needle shaft portion extending away from the front needle body in a forward direction and including a sharp front end, said internal needle cavity channel extending an entire length of said needle shaft, said front needle body including a guiding channel and a locking receptacle, said guiding channel and said locking receptacle being exposed on an outer surface of said front needle body, said locking receptacle connecting to a rear end of said guiding channel and extending away from said guiding channel in a circumferential needle detachment direction, said rear needle cap being attached to the rear needle body such that the sharp needle rear end is disposed inside the rear needle cap, the front needle cap comprising a sidewall, a front wall, an internal cavity extending within the sidewall from the front wall to a rear opening, the front needle cap sidewall having an inner side with an inwardly protruding locking plug formed thereon, the front needle cap being attached to the front needle body such that the sharp needle front end is disposed inside the front needle cap internal cavity and the locking plug of the front needle cap is disposed within the locking receptacle of the front needle body, the syringe comprising a barrel and a syringe needle adaptor at a front end of the barrel, the syringe needle adaptor having an internal channel extending from a rear end to a front end of the syringe needle adaptor, and the needle coupling mechanism being adapted for attaching the needle to the syringe needle adaptor for use of the needle with the syringe, the method comprising:

removing the rear needle cap from the rear needle body;

inserting the sharp needle rear end into the syringe needle adaptor internal channel;

rotating the front needle cap in an attachment direction relative to the syringe barrel, the attachment direction being opposite to said detachment direction, to cause the needle coupling mechanism to rotate in the attachment direction relative to the syringe needle adaptor to attach the needle to the syringe needle adaptor, and to cause the front needle cap to rotate in the attachment direction relative to the front needle body such that the locking plug is aligned with the guiding channel of the front needle body;

pulling the front needle cap forwardly away from the needle with the locking plug moving inside the guiding channel to detach the front needle cap from the front needle body; and continuing to pull the front needle cap forwardly away from the needle to remove the sharp needle front end from the front needle cap.

9. The method of claim 8, wherein the syringe is an aspirating syringe.

10. The method of claim 8, wherein said causing the front needle cap to rotate in the attachment direction relative to the front needle body is performed after the needle is attached to the syringe needle adapter by said causing the needle coupling mechanism to rotate in the attachment direction relative to the syringe needle adaptor.

11. The method of claim 10, wherein said locking plug and said locking receptacle have the same or substantially the same shape for tight interlocking.

12. The method of claim 8, wherein the needle coupling mechanism is formed in the rear needle body.

13. The method of claim 12, wherein the needle coupling mechanism is a female thread, said coupling the needle coupling mechanism to the syringe needle adaptor comprising threading the female thread onto a male thread of the syringe needle adaptor.

14. The method of claim 12, wherein the needle coupling mechanism is a clockwise thread and said attachment direction is clockwise.

15. A method of disposing of a used needle attached to a syringe, the syringe comprising a barrel having a front end and a syringe needle adaptor at the front end of the barrel, the needle comprising a needle hub and a needle shaft, said needle shaft being fixedly disposed within and running through said needle hub, said needle hub including a rear needle body and a front needle body, said needle shaft including front needle shaft portion extending forwardly from said front needle body and comprising a sharp needle front end, a rear needle shaft portion extending rearwardly from said rear needle body and comprising a sharp needle rear end, and an internal cavity channel extending an entire length of said shaft, said rear needle body being detachably attached to the syringe needle adaptor so that the rear end needle shaft portion extends into a front opening of an internal channel extending through said syringe needle adaptor, said front needle body including a guiding channel and a locking receptacle, said guiding channel and said locking receptacle being exposed on an outer surface of said front needle body, said locking receptacle connecting to a rear end of said guiding channel and extending away from said guiding channel in a needle detachment direction, the method comprising, after the needle has been used to penetrate into a patient's body and then removed from the patient's body:

inserting the sharp needle front end and the front end portion of the needle shaft through a rear opening and into an internal cavity of a front needle cap, the front needle cap comprising a sidewall and a front wall, said internal cavity extending within the sidewall from the front wall to said rear opening, said sidewall having an inner side with an inwardly protruding locking plug formed thereon;

aligning the front needle cap locking plug with the front needle body guiding channel;

moving the needle further inside the front needle cap while the locking plug moves inside the guiding channel to move the locking plug to the rear end of the guiding channel;

rotating the front needle cap in a needle detachment direction relative to the syringe barrel so as to move the locking plug from the rear end of the guiding channel into the locking receptacle and along a rearward facing first side of the locking receptacle until the locking plug is against a second side of the locking receptacle, the second side extending in a rearward direction from the first side; and continuing to rotate the front needle cap in the needle detachment direction so that the locking plug drives the needle hub to rotate in the needle detachment direction relative to the syringe needle adaptor until the rear needle body is detached from the syringe needle adaptor.

16. The method of claim 15, further comprising pulling the front needle cap forwardly away from the syringe needle adaptor to remove the needle shaft rear end portion from the internal channel of the syringe needle adaptor, inserting the sharp needle rear end into a rear needle cap, and attaching the rear needle cap to the rear needle body so that the sharp needle rear end is disposed inside the rear needle cap.

17. The method of claim 15, further comprising the rearward facing first side of the locking receptacle restraining forward movement of the locking plug while the locking plug is in the locking receptacle.

18. The method of claim 15, further comprising the needle detachment direction being counterclockwise with respect to a front end view of the syringe needle adaptor.

* * * * *